(12) United States Patent  
Kroll (10) Patent No.: US 6,351,670 B1  
(45) Date of Patent: Feb. 26, 2002

(54) ELECTRICAL CARDIAC ASSIST FOR AN IMPLANTABLE SYNCOPE MONITOR

(75) Inventor: Kai Kroll, Minneapolis, MN (US)

(73) Assignee: Galvani, Ltd., Minneapolis, MN (US)

( * ) Notice: Subject to any disclaimer, the term of this patent is extended or adjusted under 35 U.S.C. 154(b) by 0 days.

(21) Appl. No.: 09/392,233

(22) Filed: Sep. 8, 1999

Related U.S. Application Data (63) Continuation-in-part of application No. 08/754,712, filed on Dec. 6, 1996, now Pat. No. 5,978,703, which is a continuation of application No. 08/543,001, filed on Oct. 13, 1995, now abandoned, which is a continuation of application No. 08/251,349, filed on May 31, 1994, now abandoned.

(60) Provisional application No. 60/099,458, filed on Sep. 8, 1998.

(51) Int. Cl.[7] ............................................. A61N 1/39
(52) U.S. Cl. ........................................................ 607/5
(58) Field of Search ............................................. 607/5

(56) References Cited

PUBLICATIONS

DeBehnke, Daniel, "Resuscitation time limits in experimental pulseless electrical acitvity cardiac arrest using cardiopulmonary bypass," *Resuscitation* 27, pp. 221–229, Feb. 28, 1994.

Bleske, et al., "Comparison of adrenergic agonists for the treatment of ventricular fibrillation and pulseless electrical activity," *Resuscitation* 28, pp. 239–251, Aug. 1994.

Quinn, et al., "Need for Sedation in a Patient Undergoing Active Compression—Decompression Cardiopulmonary Resuscitation," *Academic Emergency Medicine*, vol. 1, No. 5, pp. 463–467, Sep./Oct. 1994.

*Primary Examiner*—William E. Kamm  
(74) *Attorney, Agent, or Firm*—Fredrikson & Byron, P.A.

(57) ABSTRACT

A method and apparatus for monitoring syncope, and having available for use an electrical cardiac output forcing (ECOF) back up. An implantable device, including an ECOF back up, for recording the electrical activity within a human heart is provided. The device includes a power supply for operating the device and for providing the necessary output forcing signals. A monitoring or detection device is provided connected to the power supply. Electrodes are provided to electrically connect the power supply and the detection device to a patient's heart. A memory device is also provided connected to the detection device for recording electrical activity and/or blood pressure data of the patient's heart. The memory device may be comprised of a short term loop buffer for continuously recording the electrical data from the patient's heart and a long term storage buffer. The short term loop may be of a desired size, for example, capable of storing from 1–30 minutes of data before overriding occurs. Upon the occurrence of a predetermined event, for example, a bout of syncope, the data in the short term loop buffer is transferred to the long term storage buffer. An output control circuit is also provided which is connected to the detection device and to the power supply and to the electrodes. Upon the occurrence of a second predetermined event, such as fibrillation of the heart, the output control circuit causes the delivery of an electrical cardiac output forcing signal to the patient's heart.

37 Claims, 7 Drawing Sheets

ELECTRICAL CARDIAC ASSIST FOR AN IMPLANTABLE SYNCOPE MONITOR

REFERENCE TO RELATED APPLICATIONS

This application is also a continuation-in-part of U.S. patent application Ser. No. 08/754,712, filed Dec. 6, 1996, now U.S. Pat. No. 5,978,703, titled "Method and apparatus for temporarily electrically forcing cardiac output in a tachyarrhythmia patient," issued Nov. 2, 1999, which is a continuation of U.S. patent application Ser. No. 08/543,001, filed Oct. 13, 1995, now abandoned, which was a continuation of U.S. patent application Ser. No. 08/251,349, filed May 31, 1994, now abandoned. It also claims benefit to U.S. Ser. No. 60/099,458 filed Sep. 8, 1998.

FIELD OF THE INVENTION

This invention generally relates to cardiac arrhythmia monitoring. In particular, the present invention pertains to a syncope monitor. Even more particularly, the present invention pertains to a syncope monitoring device that subcutaneously measures and records information regarding syncope.

BACKGROUND OF THE INVENTION

Nearly half of all Americans will have at least one episode of syncope (sudden transient loss of consciousness) in their lives. It has been estimated that as many as one million people are evaluated and treated for syncope each year in the United States at a cost to the health care industry of more than one billion dollars. More than 100,000 patients per year report to their doctors repeated episodes of syncope. Depending on the cause of the syncope, the prognosis varies from excellent to poor. There are many causes of syncope, but more than half of the episodes have a recognizable cardiovascular cause. When structural heart disease is present, syncope often signals a mechanical or electrical cardiac cause. When structural heart disease is absent, a disorder of cardiovascular reflexes is the most likely cause of syncope. Syncope can be associated with bodily injury due to falls or other accidents. Additionally, individuals who experience syncope may have a serious underlying cardiac condition and may run the risk of increased mortality or morbidity if the condition is left undiagnosed.

External ambulatory monitors that record an electrocardiography (ECG) continuously or during predetermined symptoms are often prescribed. Patients may wear such devices, such as halter monitors, for one day to several months. However, for patients whose symptoms occur infrequently, the monitoring period may not be long enough to capture a diagnostic ECG. Additionally, patient compliance with long term use of such monitors is problematic and can limit or hinder normal activities such as swimming, bathing and even dressing. Another deficiency with external monitoring devices is that many patients being monitored for syncope will suffer fibrillation and die while being monitored.

Approximately 400,000 Americans succumb to ventricular fibrillation each year. It is known that ventricular fibrillation, a usually fatal heart arrhythmia, can only be terminated by the application of an electrical shock delivered to the heart. This shock is delivered through electrodes applied to the chest and connected to an external defibrillator or through electrodes implanted within the body and connected to an implantable cardioverter defibrillator (ICD). Often times paramedics cannot respond rapidly enough with their external defibrillators to restore life. New methods of dealing with this problem including less expensive external defibrillators (and thus more readily available) and smaller implantable defibrillators are being introduced.

A typical ICD includes an electrical pulse generator and an arrhythmia detection circuit coupled to the heart by a series of two or more electrodes implanted in the body. A power supply, and one or more charge storage capacitors are used for delivering defibrillation shocks in the form of electrical current pulses to the heart. These devices try to restore normal rhythm to a fibrillating heart. While ICDs work well at restoring normal function, the ICD is expensive and large in size and not practical for a truly prophylactic device. ICDs are designed to furnish hundreds of high voltage defibrillation shocks over a period of years.

Various researchers have tried to reduce the energy thresholds required for defibrillation. For example, Kirchoff experimented with local pacing during fibrillation in dog hearts (c. 1993; 88: 736–749). Kirchoff used 0.5 mm diameter electrodes and pacing stimuli. As expected, small areas around the heart were captured but no pumping action was expected or detected. Similar results have been obtained in the ventricle by KenKnight (*Journal of the American College of Cardiology,* 1994; 283A). A number of researchers have tried multiple pulse defibrillation without success in reducing the energy thresholds. Schuder (*Cardiovascular Research;* 1970, 4, 497–501), Kugelberg (*Medical & Biological Engineering;* 1968, 6, 167–169), Resnekov (*Cardiovascular Research;* 1968, 2, 261–264), and Geddes (*Journal of Applied Physiology;* 1973, 34, 8–11). More recently, Sweeney in U.S. Pat. No. 4,996,984 experimented with multiple (primarily dual) shocks timed based on calculations from the fibrillation rate. None of the above approaches significantly reduced voltages needed to effectively defibrillate a heart.

As can be appreciated from the above, there is an acute need for a improved means of monitoring syncope. The known devices are bulky, uncomfortable, and may miss the desired event.

As stated above, there is an acute need for an improved syncope monitoring device. In particular, there is a need for a small implantable device capable of monitoring syncope and maintaining a minimal cardiac output in the event of fibrillation is needed.

SUMMARY OF THE INVENTION

The present invention comprises a method and an apparatus for monitoring syncope. In one embodiment of the present invention, the syncope monitor includes electrical cardiac output forcing (ECOF) back up. The present invention is an implantable device for recording the electrical activity within a human heart. The device of the present invention includes ECOF back up. The device includes a power supply for operating the device and for providing the necessary output forcing signals. A monitoring or detection device is connected to the power supply. The device can monitor blood pressure (BP), and record and store blood pressure readings. Electrodes electrically connect the power supply and the detection device to a patient's heart. A memory device is also provided which is connected to the detection device for recording electrical activity data of the patient's heart. In a preferred embodiment of the present invention, the memory device is comprised of a short term loop buffer for continuously recording the electrical data from the patient's heart and a long term storage buffer. The short term loop buffer may be of a desired size, for example, capable of storing from 1–30 minutes of data before overwriting occurs. Upon the occurrence of a predetermined event, for example, a bout of syncope, the data in the short term loop buffer is transferred to the long term storage buffer. An output control circuit is also provided which is connected to the detection device and to the power supply and to the electrodes. Upon the occurrence of a second predetermined event, such as fibrillation of the heart, the output control circuit causes the delivery of an electrical cardiac output forcing signal to the patient's heart.

DETAILED DESCRIPTION OF THE DRAWINGS

Figure 1:
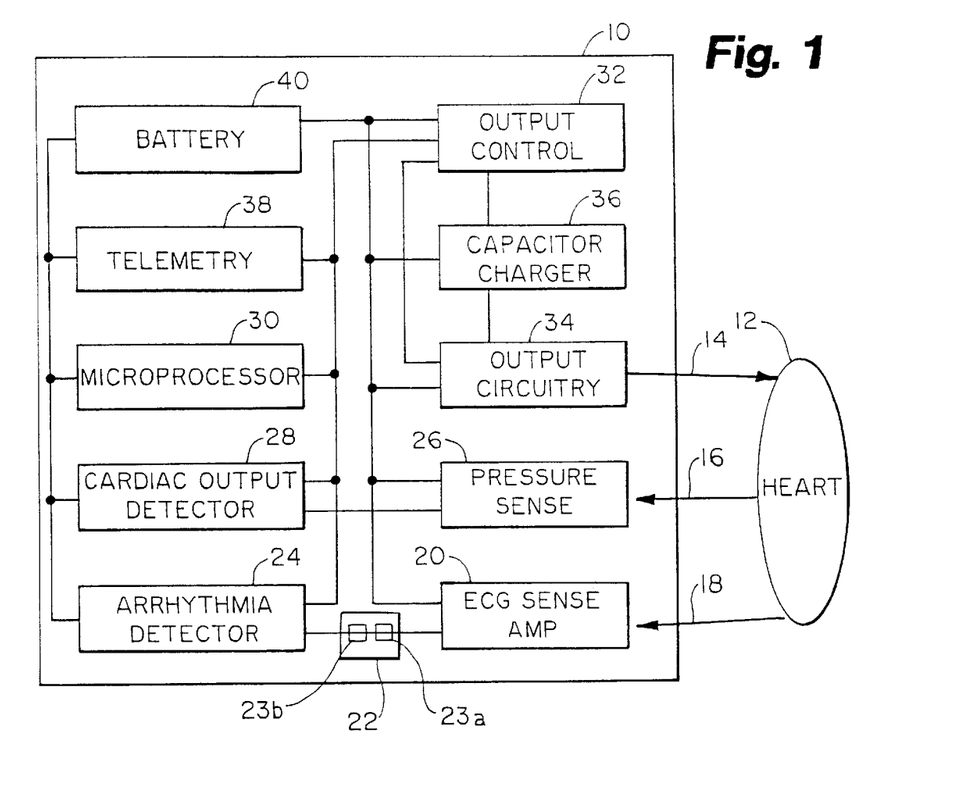
FIG. 1 is a block diagram illustrating a system constructed in accordance with a first preferred embodiment of the present invention.

The present invention comprises a syncope monitor that includes electrical cardiac output forcing (ECOF) back up. FIG. 1 is a block diagram illustrating a system 10 constructed in accordance with the present invention. System 10 is connected to a heart 12 by a series of leads including an output lead 14, an optional pressure sensing lead 16, and an ECG sensing lead 18. System 10 includes a conventional ECG amplifier 20 for amplifying cardiac signals. The amplified cardiac signals are analyzed by a syncope monitor 22 that includes a loop buffer 23a and a long term storage buffer 23b which will be described in greater detail below. The amplified cardiac signals also are analyzed by a conventional arrhythmia detector 24 which determines if an arrhythmia is present. System 10 also contains an optional pressure sensing section 26 which amplifies and conditions a signal from an optional pressure sensor from within heart 12 or an artery. The output of pressure sensor circuit 26 is fed to a cardiac output detection circuit 28 which analyzes the data and determines an estimate of cardiac output. Data from arrhythmia detector 24 and cardiac output detection circuit 28 is fed to a microprocessor 30. Microprocessor 30 determines if ECOF is appropriate. If forcing is indicated, microprocessor 30 prompts an output control 32 to charge a capacitor within an output circuit 34 via a capacitor charger 36. Output control 32 directs output circuit 34 to deliver pulses to heart 12 via output leads 14. Additionally, microprocessor 30 may communicate with external sources via a telemetry circuit 38 within device 10. The power for system 10 is supplied by an internal battery 40. In a general sense, references to ECG throughout may be interpreted as BP as well, where appropriate, as another form of sensed signal.

Figure 2:
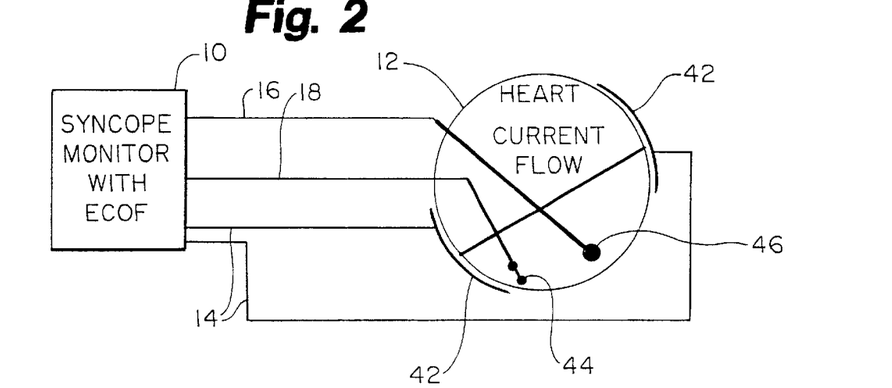
FIG. 2 is a perspective view of the system of the present invention in an epicardial patch configuration.
Figure 3:
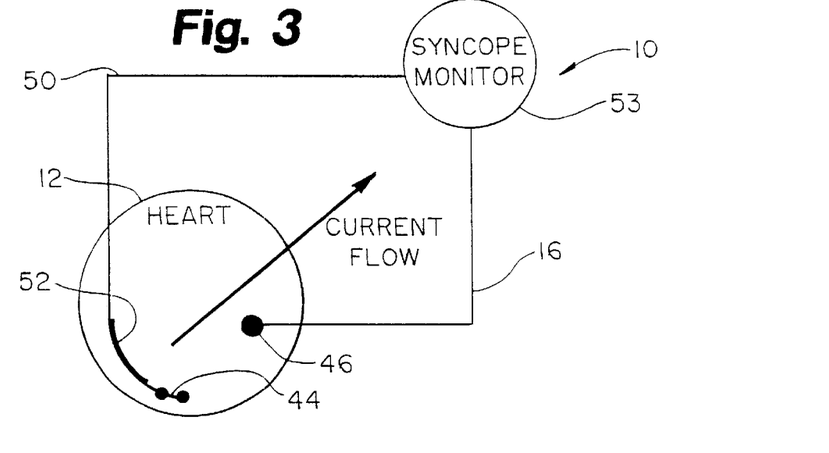
FIG. 3 is a perspective view of the system of the present invention using an endocardial lead.

FIGS. 2 and 3 illustrate various configurations of using the present invention. In FIG. 2, an epicardial patch configuration is illustrated. In FIG. 3, a non-thoracotomy system is illustrated using an endocardial lead. FIG. 2, in particular, illustrates system 10 adapted for a thoracotomy configuration wherein electrode patches 42 are attached to heart 12. Electrode patches 42 are connected to system 10 through output leads 14. Optional pressure sensing lead 16 passes a signal from an optional pressure transducer 46 which lies in heart 12. The ECG is monitored by sense electrodes 44 which is connected to system 10 by ECG sensing lead 18.

FIG. 3 illustrates a non-thoracotomy system wherein current passes from a coil electrode 52 in heart 12 to a housing 53 of system 10. An endocardial lead 50 combines ECG sensing electrodes 44 and coil electrode 52. A patient's ECG is monitored by sense electrodes 44 in heart 12 and passes the signal through endocardial lead 50. Additionally, optional pressure transducer 46 is available which passes a signal to system 10 through lead 16.

In the preferred embodiment of the present invention, syncope monitoring circuit 22 continuously monitors the heart's electrical activity and records it as a subcutaneous ECG/BP. Monitoring circuit 22 records information in a loop, replacing old ECG/BP information with new ECG/BP information. Recording information in a loop may be accomplished in a number of ways such as with a circular, or revolving buffer 23a. The buffer used for recording ECG/BP data may be of various sizes to accommodate desired recording lengths before overwriting is necessary. Preferably, loop buffer 23a will be sized to record between one and thirty minutes of data, however, greater buffer sizes may be used.

In the preferred embodiment of the present invention, after a bout of syncope has occurred, the information that has been recorded in revolving buffer 23a is transferred to a more permanent buffer 23b in syncope monitoring circuit 22. The transmission of data from revolving buffer 23a to long term storage buffer 23b may be activated by a number of protocols. For example, an external device may be used to send a command to telemetry circuit 38 instructing syncope monitoring circuit 22 to transfer the data. Syncope monitoring circuit 22 may be programmed to automatically transfer data to buffer 23b after an event has been detected, or syncope monitoring circuit 22 may be equipped with a magnetically actuated switch (not shown) which causes the transfer of data from buffer 23a to buffer 23b when a magnet is placed in proximity to the patient's chest. It should be noted that these are only a few examples and this list is not meant to be exhaustive.

Long term buffer 23b is preferably sized larger than loop buffer 23a. By sizing long term storage buffer 23b larger than loop buffer 23a, data recording multiple syncope events can be transferred from loop buffer 23a and stored in buffer 23b before buffer 23b is full. Storing multiple syncope events may be important if the patient is not able to get to a physician immediately after the first recorded occurrence of syncope.

Figure 4:
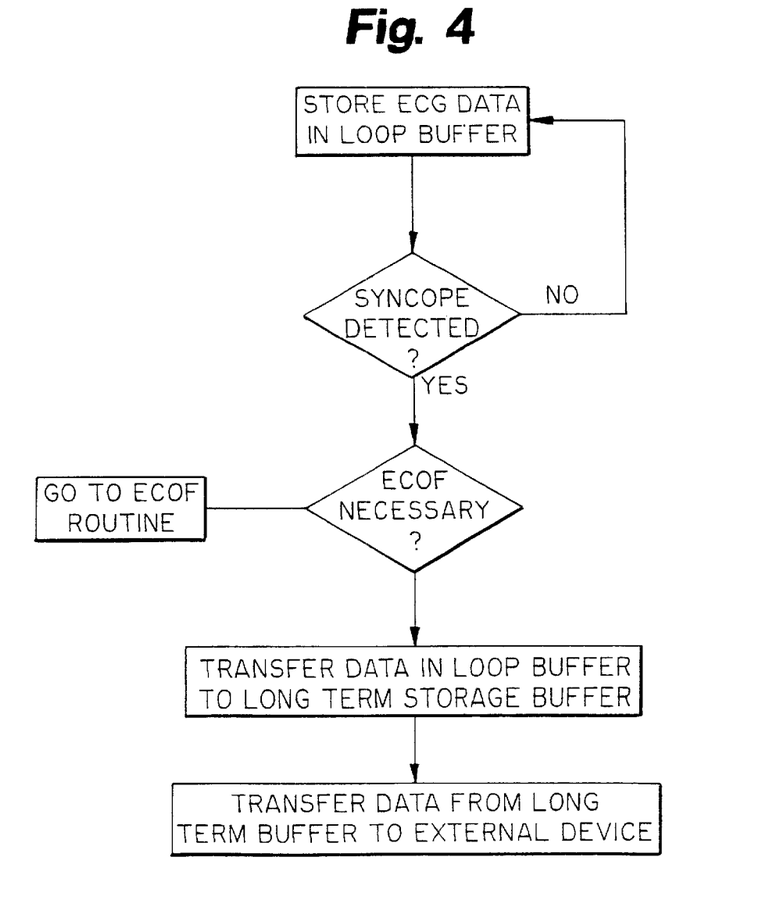
FIG. 4 is a flow chart illustrating the syncope monitoring portion of the present invention.

After the data has been transferred to long term storage buffer 23b, the data is available for downloading to an external device for analysis by doctors. The external device (not shown) may be a portable hand held device used by the patient or a larger device used in hospitals or clinics. The data may be downloaded from storage buffer 23b to the external device via telemetry circuit 38. Data may be downloaded upon command from the external device, or, as with the transfer from buffer 23a to buffer 23b, with the aid of a magnet switch that is activated by a separate magnet or a magnet located in the external device. A flow chart of the syncope monitoring portion of the preferred embodiment of the present invention is illustrated in FIG. 4.

In an alternative embodiment of the present invention, syncope monitoring circuit 22 only begins recording the subcutaneous ECG signals when an indicia of syncope has been detected. In this embodiment, loop buffer 23a is not recording anything until such indicia of syncope is first detected. At that point, ECG data is recorded in loop buffer 23a. This alternative embodiment is not as desirable as the preferred embodiment which continuously records ECG data in loop buffer 23a, because in this embodiment the ECG signals, prior to the first indicia of syncope, will not be recorded and therefore will be unavailable for comparison.

The present invention also includes backup ECOF functionality. If ventricular fibrillation is sensed by arrhythmia detector circuit 24, ECOF pulses will be delivered to the heart to maintain life until external defibrillation therapy is administered.

As stated above, the goal of ECOF is maintaining some cardiac output yet not necessarily defibrillation. To accomplish this, a forcing field is generated by applying approximately 50 V to the heart at a rate of approximately 100–180 beats per minute. These fields are applied after detection of an arrhythmia and maintained for up to several hours. This will generate a cardiac output which is a fraction of the normal maximum capacity. The heart has a four or five times reserved capacity so this fraction of the normal pumping activity will maintain life and consciousness to allow a patient enough time to get to a hospital. The patient would then be a candidate for an implantable cardioverter defibrillator.

Figure 5:
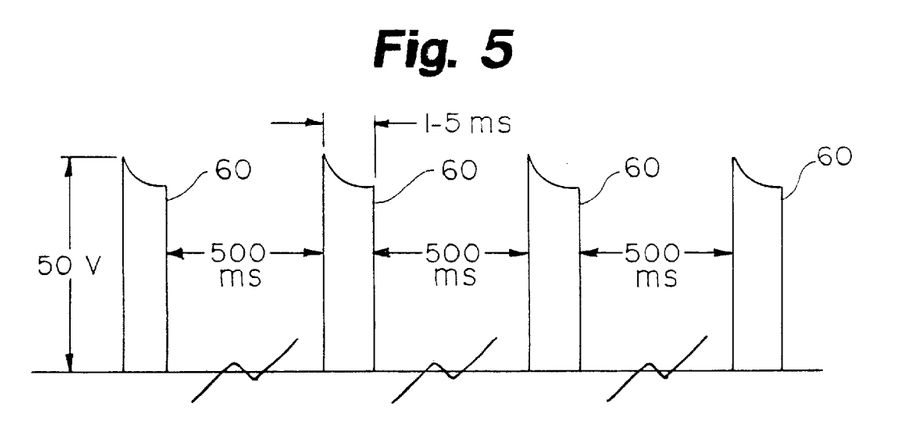
FIG. 5 is a diagram showing a representative electrical signal of the present invention.

A series of forcing pulses 60 are shown in FIG. 5. The pulses are approximately 50 V in amplitude with a spacing of approximately 500 ms. The 50 V and 500 ms pulse spacing are chosen as illustrative for an implantable device. The forcing pulse interval is chosen to maximize cardiac output within the limits of device circuitry and the response of the heart muscle. An interval of 500 ms corresponds to a heart rate of 120 beats per minute. However, a rate of 240 beats per minute would produce a lower output due to mechanical limitations of the heart. Thus, a practical range is 60 to 200 beats per minute. The pulses could also be timed to coincide with the natural pumping of the atria, thus improving overall cardiac output.

The higher the voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50 ohms, the power during the pulse is $P=V^2/R=50V/50\Omega=50$ W. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes (10,000 J/4.8 W=2083 seconds). Thirty-five minutes may not be enough time to transport the patient to a hospital. Therefore, 200 V represents the highest practical voltage for continuous operation in an implantable device, although voltages of up to 350 V could be used for short periods and reduced downwardly when hemodynamic output is verified. A practical lower limit is about 10 V. During normal sinus rhythm, a 10 V signal delivered through the patches would pace. However, during fibrillation the 10 V signal could not pace and only cells very near the electrodes would be captured. This 10 V signal would be insufficient for forcing cardiac output.

These calculations also suggest other differences between an implantable ECOF and an ICD. With a battery storing 10,000 J and ECOF pulse having 0.1 J, this ECOF would be capable of delivering 100,000 pulses. An ICD can only deliver 200–4300 shocks of about 30 J. The ECOF is also very different from an implantable pacemaker which typically delivers 150,000,000 pacing pulses (5 years at 60 BPM) each of about 0.00005 J.

Figure 6:
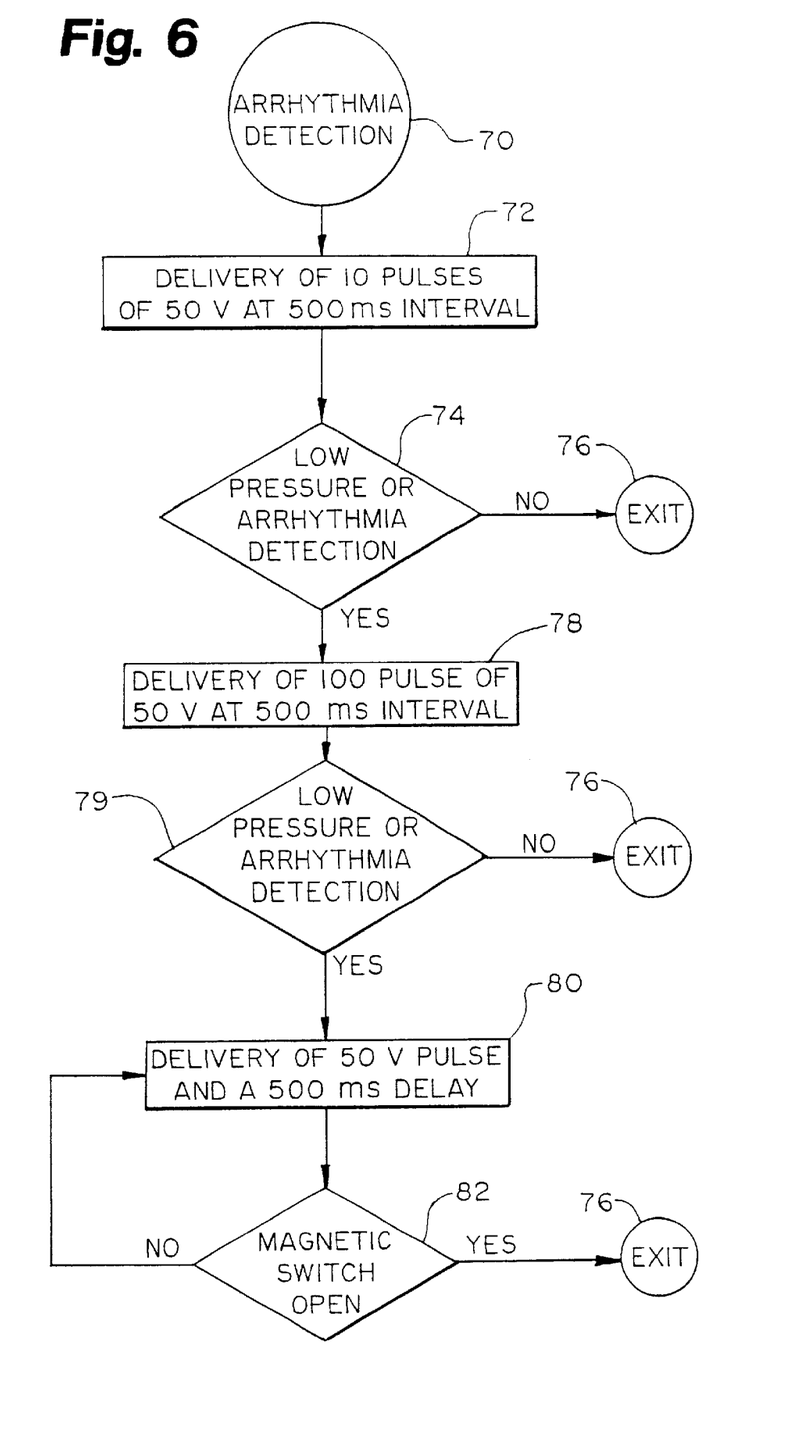
FIG. 6 is a flow chart illustrating the ECOF portion of the present invention.

FIG. 6 is a flow chart illustrating a method of applying ECOF pulses according to the present invention. It should be noted that this chart is provided for purposes of illustration only and that one skilled in the art will recognize from the discussion that alternative methods may be employed without departing from the principles of the invention. The flow chart shown in FIG. 6 represents a method of automatically treating a heart which is in fibrillation, tachycardia, or asystole and thereby pumping inefficiently or not at all. Once an arrhythmia is detected in block 70, a series of cardiac output forcing electric pulses are automatically delivered in block 72. It should be understood that the therapy may be delivered for any output compromising cardiac arrhythmia. After delivery often forcing pulses (at a rate of 60–200 BPM) block 72, the status of the heart is determined in block 74. If an arrhythmia is still present and there exists low pressure within the heart, more forcing pulses are delivered in block 78. If the heart is pumping at a safe level, the therapy ceases and exits at block 76. Note that this means that the ECOF successfully defibrillated the patient's heart even though this is not a primary goal of the system. For those patients who are defibrillated by ECOF pulse therapy, it is possible they could then receive ECOFs instead of the larger ICD. After the therapy in block 78 has been delivered, the pressure and ECG is again monitored in block 79. If the therapy is successful, it ceases and exits in block 76. If the therapy from block 78 is unsuccessful in producing a safe level of pumping efficiency, the method proceeds to a continuous cardiac assist mode as in block 80. This therapy may only be stopped by an external command, for example, a telemetry signal or a magnet which is applied to the chest activating a magnetic reed switch as indicated in block 82 which terminates the therapy and exits in block 76. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

Figure 7:
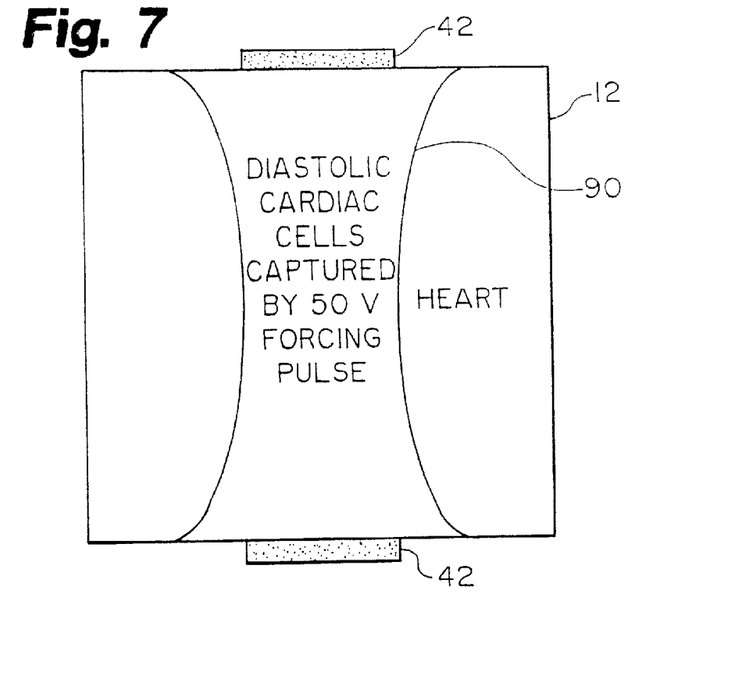
FIG. 7 is a diagram showing the expected effect of a 50 volt pulse on a heart during diastole.

FIG. 7 is a diagram showing the effect of a 50 V forcing pulse of heart 12 during electrical diastole (cells at rest). The current is passed through heart 12 by electrodes 42. Approximately 60% of cardiac cells 90 would be captured by a 50 V pulse if the cells were is diastole. Captured cells 90 mostly lie in the direct path between electrodes 42 and near electrodes 42 where the field strengths are highest. Of course, over a time period of about 100 ms these directly captured cells then propagate an activation wavefront to stimulate the rest of the heart. This so called far-field pacing is irrelevant here as the hearts, of interest, are in fibrillation and not in diastole.

Figure 8:
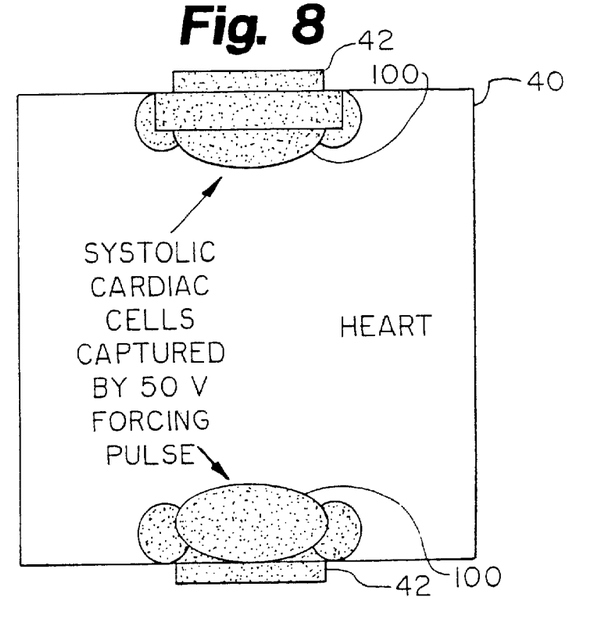
FIG. 8 is a diagram showing the expected effect of a 50 volt pulse on a heart during systole.

FIG. 8 is a diagram showing the effect of a 50 V forcing pulse on the heart during electrical systole (cells already stimulated). The current is passed through heart 12 by electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (10 V/cm) than those required for diastolic cell capture (1 V/cm).

Figure 9:
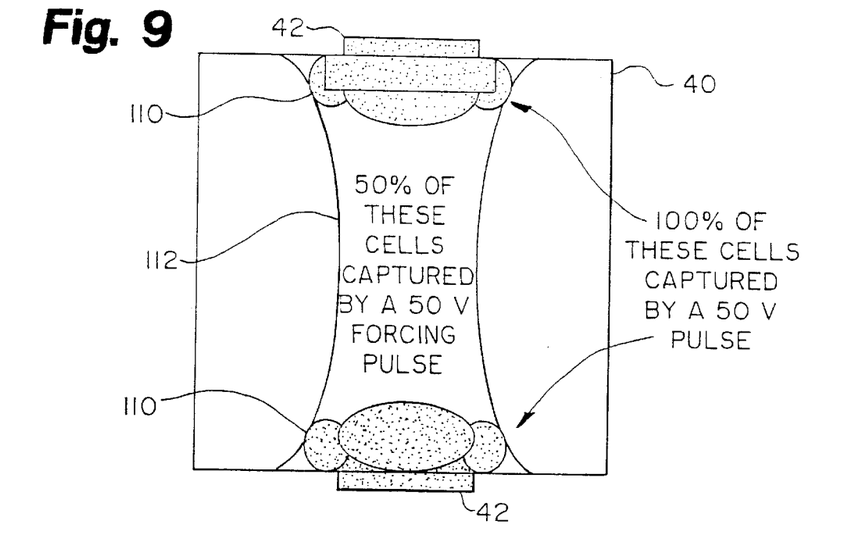
FIG. 9 is a diagram showing the expected effect of a 50 volt pulse on a heart during fibrillation.

FIG. 9 is a diagram showing the effect of a 50 V forcing pulse on the heart during fibrillation. During fibrillation there are always cells in systole and diastole simultaneously. But, the vast majority are in systole. This diagram assumes 50% of the cells are in diastole which applies only after several capturing pulses. The current is passed through heart 12 by electrodes 42. One hundred percent of the cells 110 nearest electrodes 42 would be captured due to the high field strength. As shown in FIG. 8, even systolic cells are captured by high field strengths. Fifty percent of cells 112 in the direct path between electrodes 42 would be captured if it is assumed that 50% of all cells are in diastole. If roughly 60% of cardiac cells are captured by a 50 V pulse when the cells are in diastole, and 20% are captured when in-systole, and if 50% are in systole and 50% in diastole, 40% would be captured during fibrillation. This calculation is shown in the following table. The last two columns give the mechanical action resulting and the contribution to forcing a cardiac output. Considering the cardiac cells that are originally in diastole, (rows A & B) in the table below, the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next considering the activity of the systolic cells (rows C & D), if 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result is a gain in contraction which forces cardiac output.

| Original status of the cells | Percentage of the cardiac cells | Status of the cardiac cells | Percentage of the original status | Percentage of the total cells | Mechanical Action | Forcing Cardiac Output Effect |
|---|---|---|---|---|---|---|
| (A) Diastolic | 50% | Diastolic non-captured | 40% of 50% | 20% | will start to contract on own | positive (+) |
| (B) Diastolic | | Diastolic captured | 60% of 50% | 30$ | contract | positive (++) |
| (C) Systolic | 50% | Systolic non-captured | 80% of 50% | 40% | will start to relax on own | negative (−) |
| (D) Systolic | | Systolic captured | 20% of 50% | 10% | hold | neutral (0) |
| Total | 100% | | 100% | 100% | more contraction | positive (++) |

The net result over a 200 ms mechanical response is given in the next table. The major contribution is in row (B) from the captured diastolic cells contracting.

| Row | Status of the Cardiac Cells | Change in Output | Description of Activity |
|---|---|---|---|
| A | Diastolic non-captured | +5% | Positive. Some cells will begin to contract on their own. |
| B | Diastolic captured | +30% | Positive. Cells contract due to forcing field. |
| C | Systolic non-captured | −5% | Negative. Some cells will begin to relax on their own. |
| D | Systolic captured | 0% | Neutral. Cells hold contraction due to forcing field. |
| Net Gain | | +30% | A net gain in cardiac output due to forcing fields. |

The 30% net pumping action should be sufficient to maintain survival and consciousness, because the heart has a 4–5 times reserve capacity.

Figure 10:
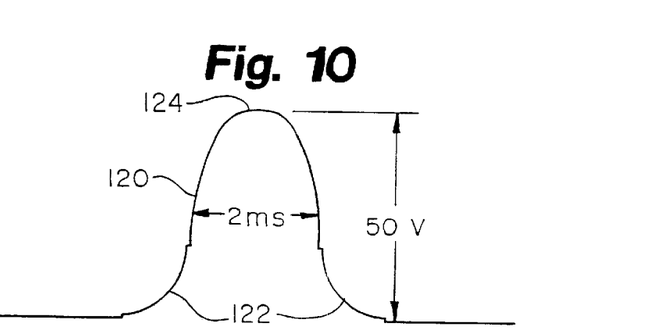
FIG. 10 illustrates a waveform useful for the electrical cardiac output forcing function.
Figure 11:
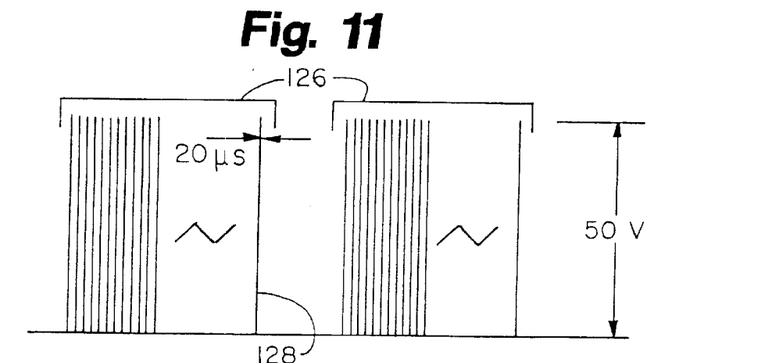
FIG. 11 illustrations an alternative waveform useful for the electrical cardiac output forcing function.

FIGS. 10 and 11 depict examples of waveforms designed to minimize the twitching of the chest muscles which can be very uncomfortable to the patient. In FIG. 10 a low harmonic pulse waveform 120 which has a very gradual "foot" 122 and a gradual peak 124 is illustrated. Such a pulse has less high frequency energy components and thus is less likely to stimulate the skeletal muscle.

FIG. 11 shows the opposite extreme. Here, each compound forcing pulse 126 is actually composed of 50 very short spikes 128 each of which is 20 As in width with a 20 μs spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

An alternative system would be to initially apply a 300 V pulse to capture many cells therefore putting those cells into diastole after a delay of 100–200 ms. At this point, the voltage could be lowered to 100 V and delivered every 100 ms. A 3 watt DC-DC converter with a 67% efficiency could provide 100 ms interval forcing pulses assuming a 50 ohm resistance and 1 ms pulse (0.2 J). This rate is too fast for forcing cardiac output due to mechanical limitations, but is very effective for electrical capture. After sufficient capture, the rate of forcing pulses could be slowed down to 100–170 beats per minute for optimum cardiac output.

The Electrical Cardiac Output Forcing (ECOF) portion of the present invention could also be used to help patients with atrial fibrillation. As an alternative embodiment to the ventricular placement of FIG. 3, electrode coil 52 and sensing electrodes 44 could be placed in the atrium. The device could then function to force atrial output. Even though atrial fibrillation is not instantly fatal like ventricular fibrillation, clots can build up in the atria which can eventually lead to strokes. Cardiac output forcing of the atria on a daily basis may limit this problem. It is also possible that after a number of forcing pulses the atria would return to a normal rhythm. There is, however, no urgency as is the case with ventricular fibrillation.

Figure 12:
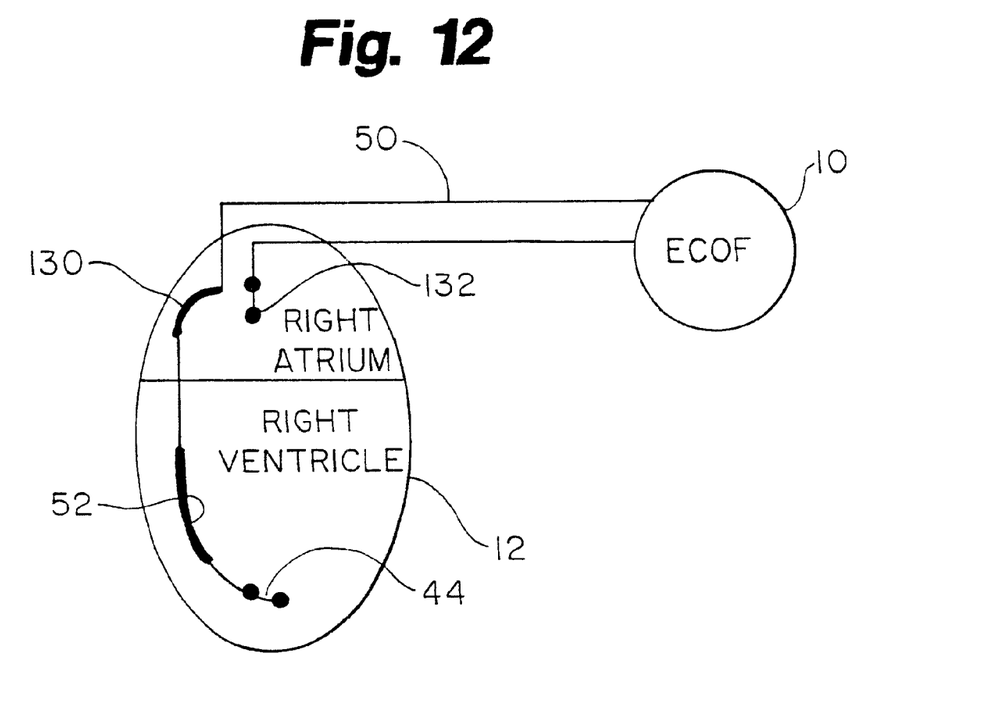
FIG. 12 is a perspective view of the system of the present invention in an alternative embodiment.

FIG. 12 illustrates a further use for the ECOF portion of the present invention. As before in FIG. 3, device 10 is shown connected to heart 12 via endocardial lead 50. Again, forcing coil electrode 52 and sensing electrodes 44 are in the right ventricle. In addition, a large atrial coil electrode 130 and atrial sensing electrodes 132 are in the right atrium. These would be used for conventional atrial defibrillation. One of the big concerns with atrial defibrillation is that in a few cases, an atrial defibrillation shock causes ventricular fibrillation. If this happens, the patient dies within minutes. In this embodiment, the present invention could maintain output in the patient for several hours and thus have enough time for transport to a hospital for external defibrillation. Thus, the ECOF approach in the ventricle could provide a safety back up to atrial defibrillation.

It should be understood that various alternatives to the embodiments of the invention described herein may be employed in practicing the invention. For example, while most of the discussion is in the context of an implantable device, the concepts of the invention are also applicable to external delivery systems. It is intended that the following claims define the scope of the invention and that structures and methods within the scope of these claims and their equivalents be covered thereby.

What is claimed is:

1. An implantable device for recording electrical activity within a heart wherein the device includes electrical cardiac output forcing back up, the device comprising:
   power supply means;
   detection means connected to the power supply means;
   means to communicatively connect the power supply means and the detection means to a patient's heart;
   memory means operably connected to the detection means for recording electrical activity data of the patient's heart upon the occurrence of a first predetermined condition; and
   output control means connected to the detection means and to the power supply means and to the means to communicatively connect for delivering an electrical cardiac output forcing signal to the patient's heart upon the occurrence of a second predetermined condition.

2. The device as in claim 1, wherein the detection means comprises an ECG sensor.

3. The device as in claim 1, wherein the means to communicatively connect comprises at least one electrode.

4. The device as in claim 3, wherein the at least one electrode is insertable into the patient's heart.

5. The device as in claim 1, wherein the memory means comprises first and second memory buffers.

6. The device as in claim 5, wherein the first memory buffer is a short term revolving buffer.

7. The device as in claim 6, wherein the short term revolving buffer records less than 30 minutes of electrical activity data.

8. The device as in claim 5, wherein the second memory means buffer is a long term buffer operably coupled to the short term buffer.

9. The device as in claim 8, wherein the long term buffer records more than 30 minutes of electrical activity data transferred to it from the short term buffer.

10. The device as in claim 8, further comprising downloading means for downloading data in the long term buffer to an external device.

11. The device as in claim 1, wherein the first predetermined condition is the detection of syncope.

12. The device as in claim 1, wherein the second predetermined condition is ventricular fibrillation.

13. The device as in claim 1, wherein the electrical cardiac output forcing signal has a voltage between 25 and 200 volts and a current greater than 250 mA.

14. An implantable device for recording electrical activity within a heart wherein the device includes electrical cardiac output forcing back up, the device comprising:
   power supply means;
   detection means connected to the power supply means;
   means to communicatively connect the power supply means and the detection means to a patient's heart;
   memory means operably connected to the detection means for continuously recording electrical activity data of the patient's heart; and
   output control means connected to the detection means and to the power supply means and to the means to communicatively connect for delivering an electrical cardiac output forcing signal to the patient's heart upon the detection of fibrillation.

15. The device as in claim 14, wherein the detection means comprises ECG sensor.

16. The device as in claim 14, wherein the means to communicatively connect comprises at least one electrode.

17. The device as in claim 1, wherein the memory means comprises first and second memory buffers.

18. The device as in claim 17, wherein the first memory buffer is a loop buffer for continuously storing the electrical activity data in a revolving loop.

19. The devices as in claim 18, wherein the loop buffer records less than 30 minutes of electrical activity data before overwriting occurs.

20. The device as in claim 18, further comprising data transferring means for transferring the recorded data from the first memory means to the second memory means upon the occurrence of a predetermined condition.

21. The device as in claim 20, wherein the predetermined condition is the detection of syncope.

22. The device as in claim 20, wherein the predetermined condition is the detection of a magnetic field.

23. The device as in claim 20, wherein the second memory means is capable of recording more than 30 minutes of electrical activity data received from the loop buffer.

24. The device as in claim 14, wherein the electrical cardiac output forcing signal has a voltage between 25 and 200 volts and a current greater than 250 mA.

25. An implantable cardiac device comprising:

an ECG detector having a continuous ECG recorder; and an electrical cardiac output forcing stimulator connected to the ECG detector actuable upon the occurrence of an abnormal sinus rhythm.

26. An implantable cardiac device comprising:

an ECG detector having an ECG recorder actuable upon the occurrence of a first predetermined cardiac event; and an electrical cardiac output forcing stimulator connected to the ECG detector actuable upon the occurrence of a second predetermined cardiac event.

27. A method of monitoring syncope in an implantable device having ECOF back up through electrodes connected to a power source, the method including the steps of:

monitoring a patient's heart data;

continuously recording the monitored data in a revolving buffer;

transferring the recorded data from the revolving buffer to a long term storage buffer upon the occurrence of a first event; and discharging energy from the power source across the electrodes for electrical cardiac output forcing of the heart upon the occurrence of a second event.

28. The method as in claim 27, wherein the first event is the onset of syncope.

29. The method as in claim 27, wherein the second event is the onset of fibrillation.

30. The method of claim 27, further including the step of downloading the stored data in the long term storage buffer to an external device upon a third event.

31. The method as in claim 27, wherein the first event is the detection of a magnetic field.

32. The method as in claim 30, wherein the third event is the detection of a magnetic field.

33. The method as in claim 27, wherein the step of discharging is accomplished with an energy source having a voltage between 25 and 200 volts and a current greater than 250 mA.

34. A method for maintaining cardiac equilibrium comprising;

internally monitoring a cardiac rhythm;

recording the cardiac rhythm upon the occurrence of a first predetermined cardiac event; and electrically forcing cardiac output upon the occurrence of a second predetermined cardiac event.

35. A method for maintaining cardiac equilibrium comprising:

internally monitoring and recording cardiac rhythm continuously; and electrically forcing cardiac output upon the occurrence of an abnormal sinus rhythm.

36. The device as in claim 1, wherein the detection means comprises a blood pressure monitor.

37. The method of claim 35, wherein the step of electrically forcing cardiac output is initiated by a voluntary patient prompt.

* * * * *